US009710936B2

(12) United States Patent
Schretter et al.

(10) Patent No.: US 9,710,936 B2
(45) Date of Patent: Jul. 18, 2017

(54) METHOD AND APPARATUS FOR LARGE FIELD OF VIEW IMAGING AND DETECTION AND COMPENSATION OF MOTION ARTIFACTS

(71) Applicant: KONINKLIJKE PHILIPS N.V., Eindhoven (NL)

(72) Inventors: Colas Schretter, Grez-Doiceau (BE); Matthias Bertram, Aachen (DE); Christoph Neukirchen, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/856,713

(22) Filed: Sep. 17, 2015

(65) Prior Publication Data
US 2016/0005194 A1 Jan. 7, 2016

Related U.S. Application Data

(62) Division of application No. 13/145,128, filed as application No. PCT/IB2009/055951 on Dec. 23, 2009, now abandoned.
(Continued)

(51) Int. Cl.
*G06K 9/00* (2006.01)
*A61B 6/00* (2006.01)
(Continued)

(52) U.S. Cl.
CPC ............ *G06T 11/005* (2013.01); *A61B 6/032* (2013.01); *A61B 6/4085* (2013.01);
(Continued)

(58) Field of Classification Search
CPC .... G61B 6/00; G06T 7/00; G06T 5/00; G06K 9/00
(Continued)

(56) References Cited

U.S. PATENT DOCUMENTS

| 4,150,293 A | 4/1979 | Franke |
| 4,670,892 A | 6/1987 | Abele et al. |

(Continued)

FOREIGN PATENT DOCUMENTS

| CN | 1865954 A | 11/2006 |
| GB | 2422759 A | 8/2006 |

(Continued)

OTHER PUBLICATIONS

Schaefer, D., et al.; Motion-Compensated and Gated Cone Beam Filtered Back-Projection for 3-D Rotational X-ray Angiography; 2006; IEEE Trans. on Medical Imaging; 25(7)898-906.
(Continued)

*Primary Examiner* — Abolfazl Tabatabai

(57) ABSTRACT

A method and apparatus are provided to improve large field of view CT image acquisition by using at least two scanning procedures: (i) one with the radiation source and detector centered and (ii) one in an offset configuration. The imaging data obtained from both of the scanning procedures is used in the reconstruction of the image. In addition, a method and apparatus are provided for detecting motion in a reconstructed image by generating a motion map that is indicative of the regions of the reconstructed image that are affected by motion artifacts. Optionally, the motion map may be used for motion estimation and/or motion compensation to prevent or diminish motion artifacts in the resulting reconstructed image. An optional method for generating a refined motion map is also provided.

19 Claims, 9 Drawing Sheets

Related U.S. Application Data

(60) Provisional application No. 61/146,093, filed on Jan. 21, 2009.

(51) Int. Cl.
  G06T 11/00 (2006.01)
  A61B 6/03 (2006.01)
  G06T 5/20 (2006.01)
  G06T 7/20 (2017.01)

(52) U.S. Cl.
  CPC .......... *A61B 6/4233* (2013.01); *A61B 6/4452* (2013.01); *A61B 6/488* (2013.01); *A61B 6/5217* (2013.01); *A61B 6/542* (2013.01); *A61B 6/587* (2013.01); *G06T 5/20* (2013.01); *G06T 7/20* (2013.01); *G06T 2207/10116* (2013.01); *G06T 2207/20032* (2013.01); *G06T 2211/40* (2013.01); *G06T 2211/412* (2013.01)

(58) Field of Classification Search
  USPC ............ 382/128–134; 378/4, 8, 21–27, 901; 600/407, 410, 411, 425, 427; 348/155, 348/169
  See application file for complete search history.

(56) References Cited

U.S. PATENT DOCUMENTS

| | | | |
|---|---|---|---|
| 4,847,909 A | 7/1989 | Shibata | |
| 5,032,990 A | 7/1991 | Eberhard et al. | |
| 5,233,518 A | 8/1993 | King et al. | |
| 5,319,693 A | 6/1994 | Eberhard et al. | |
| 5,640,462 A | 6/1997 | Sato et al. | |
| 6,463,118 B2 * | 10/2002 | Besson | A61B 6/032 378/15 |
| 6,546,068 B1 | 4/2003 | Shimura | |
| 7,062,006 B1 | 6/2006 | Pelc et al. | |
| 7,108,421 B2 | 9/2006 | Gregerson et al. | |
| 7,113,569 B2 * | 9/2006 | Okumura | A61B 6/032 378/150 |
| 7,251,307 B2 | 7/2007 | Chen | |
| 7,272,205 B2 * | 9/2007 | Thibault | A61B 6/032 378/4 |
| 7,630,528 B2 * | 12/2009 | Kohler | G06T 11/006 378/4 |
| 7,783,096 B2 * | 8/2010 | Chen | A61B 6/00 382/128 |
| 2002/0154728 A1 | 10/2002 | Morita et al. | |
| 2003/0063703 A1 | 4/2003 | Moore | |
| 2004/0013225 A1 | 1/2004 | Gregerson et al. | |
| 2004/0101093 A1 | 5/2004 | Matsumoto | |
| 2004/0179643 A1 | 9/2004 | Gregerson et al. | |
| 2005/0190878 A1 | 9/2005 | De Man et al. | |
| 2005/0213705 A1 | 9/2005 | Hoffman | |
| 2005/0226363 A1 | 10/2005 | Edie et al. | |
| 2005/0265523 A1 | 12/2005 | Strobel | |
| 2006/0140482 A1 | 6/2006 | Koehler | |
| 2007/0183559 A1 | 8/2007 | Hempel | |
| 2007/0268994 A1 | 11/2007 | Chen | |
| 2008/0089468 A1 | 4/2008 | Heigl et al. | |
| 2008/0123804 A1 | 5/2008 | De Man et al. | |

FOREIGN PATENT DOCUMENTS

| | | |
|---|---|---|
| JP | 9327453 A | 12/1997 |
| JP | 11009583 A | 1/1999 |
| JP | 2004136021 A | 5/2004 |
| JP | 2005334230 A | 12/2005 |
| WO | 0062674 A1 | 10/2000 |
| WO | 2007020318 A2 | 2/2007 |

OTHER PUBLICATIONS

Schretter, C., et al.; Correction of Some Time-Dependent Deformations in Parallel-Beam Computed Tomography; 2008; IEEE Trans. on Biomedical Imaging from Nano to Macro; pp. 764-767.

\* cited by examiner

METHOD AND APPARATUS FOR LARGE FIELD OF VIEW IMAGING AND DETECTION AND COMPENSATION OF MOTION ARTIFACTS

CROSS REFERENCE TO RELATED APPLICATIONS

This application is a divisional application of U.S. application Ser. No. 13/145,128 filed Jul. 19, 2011, which is a national filing of PCT/IB2009/055951 filed Dec. 23, 2009 and published as WO2010/084389 A1 on Jul. 29, 2010, which claims the benefit of U.S. provisional application No. 61/146,093, filed Jan. 21, 2009, which is incorporated herein by reference.

DESCRIPTION

The present application relates generally to the imaging arts. In one embodiment, it provides a method and apparatus for imaging large objects. In another embodiment, it provides for the detection and compensation of motion artifacts when reconstructing tomographic images. The application subject matter finds use at least with computed tomography (CT) imaging, and more particularly with flat detector cone-beam computed tomography (CBCT) imaging, and will be described with particular reference thereto. However, it also has more general application with other imaging methods and in other arts.

A conventional CT imaging device includes an x-ray source and an x-ray sensitive detector disposed on opposite sides of an examination region. A human patient or other object to be examined is supported in the examination region by a suitable support. The source emits x-ray radiation which transverses the examination region and is detected by the detector as the source and detector rotate about a center of rotation. A CT imaging device capable of having an offset geometry includes an x-ray source and an x-ray sensitive detector that may be transversely displaced from the center of rotation in the transaxial plane in certain configurations. Such offset geometry CT imaging devices are desirable because they allow for an increased field of view or allow for the use of a smaller sized detector.

However, existing offset geometry CT imaging devices may not adequately accommodate certain large objects, such as an obese patient. In part that is because x-ray source and detector offsets may deteriorate the quality of the reconstructed image. Furthermore, attenuation correction during reconstruction benefits from full anatomical coverage, which may not be possible even with large offsets.

Furthermore, the quality of images obtained from CT imaging devices, especially slowly rotating CBCT imaging devices, is also frequently degraded by uncontrolled patient movement, such as the patient's failure to hold his or her breath, intestinal contractions, nervous shaking, natural cyclic motion, heartbeat, respiration, or other forms of motion. Currently, iterative algorithmic motion compensation methods are used to improve image quality for images that contain motion artifacts. While such methods are capable of improving image quality for certain types of motion, the motion compensation effects accomplished by these methods are often inaccurate and they also can introduce artifacts into image regions that have not been affected by any motion.

It is desirable to provide a method and apparatus that permit a larger field of view than current CT imaging devices with offset geometries and that alleviate the artifacts that typically occur in reconstructed images obtained from existing CT imaging devices with large offset geometries. Further, it is also desirable to provide a method and apparatus for detecting image regions that are affected by motion artifacts when reconstructing tomographic images and for providing motion estimation and motion compensation to prevent such motion artifacts in the resulting reconstructed image.

Aspects of the present invention address these matters, and others.

According to one aspect of the present invention, a method and apparatus are provided to improve large field of view CT image acquisition using two scanning procedures: (i) one with the radiation source and detector centered and (ii) one with the detector being offset. In accordance with this aspect, a large field of view can be achieved that can accommodate larger objects than can currently be accommodated by existing CT imaging devices with offset geometries. In addition, as the imaging data from both of the scanning procedures is used in the reconstruction of the image, the artifacts that typically occur with reconstruction of imaging data obtained from existing CT imaging devices with large offset geometries can be avoided because of the large overlap between virtual detectors in opposite viewing directions.

According to another aspect of the present invention, a method and apparatus are provided for the detection and compensation of motion artifacts when reconstructing tomographic images. In accordance with this aspect, a method and apparatus for creating a motion map is provided. The motion map is utilized to indicate which image regions may be corrupted by motion artifacts and/or for motion compensation to prevent motion artifacts in the reconstructed tomographic image.

Still further aspects of the present invention will be appreciated by those of ordinary skill in the art upon reading and understanding the following detailed description. Numerous additional advantages and benefits will become apparent to those of ordinary skill in the art upon reading the following detailed description of preferred embodiments.

The invention may take form in various components and arrangements of components, and in various process operations and arrangements of process operations. The drawings are only for the purpose of illustrating preferred embodiments and are not to be construed as limiting the invention.

One aspect of the present invention is directed generally to a method and apparatus for CT image acquisition, and more particularly to a method and apparatus for providing a large field of view ("FOV") with improved image quality by utilizing at least two scanning procedures taken by a CT image apparatus. At least one scan is taken with the radiation source and detector of the CT image apparatus in a centered geometry and at least one scan is taken with the detector and/or source in an offset geometry. The image data obtained from the at least two scanning procedures is then combined to produce a reconstructed image.

Figure 1:
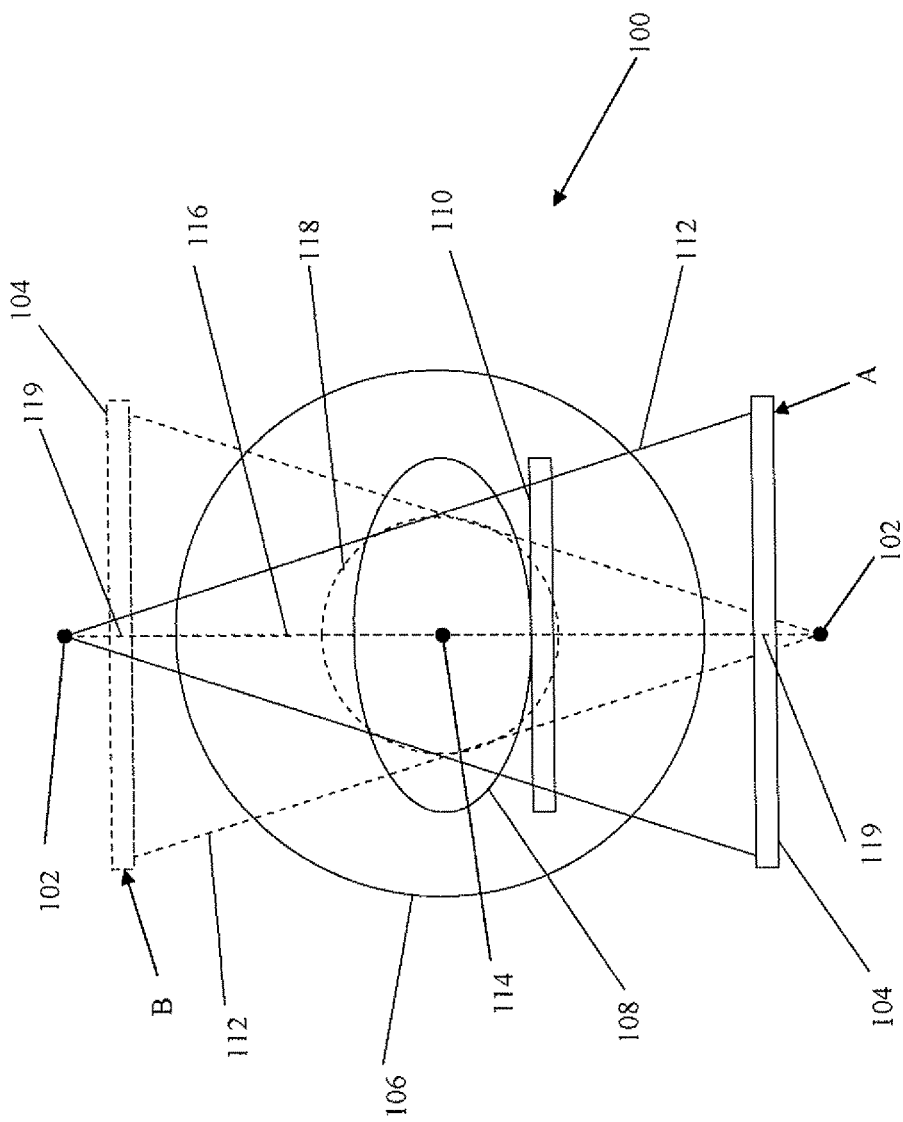
FIG. 1 is a transaxial view of a centered CT acquisition geometry according to an embodiment of the invention.

FIG. 1 depicts an exemplary centered geometry 100 for a CT imaging apparatus. The exemplary centered geometry 100 has an x-ray source 102, such as an x-ray tube, and an x-ray sensitive detector 104, such as a flat panel area detector array extending in the transverse and axial directions. As illustrated in FIG. 1, the center of rotation 114 may also serve as the center of the transverse field of view (FOV) 118. However, the center of rotation 114 is not necessarily always aligned with the center of the transverse FOV 118 in every application. As illustrated, an object support 110 supports the object 108 under examination in an examination region 106. A central ray or projection 116 of the x-ray beam 112 is perpendicular to the detector center 119, which is aligned with the center of rotation 114.

The x-ray source 102 and the x-ray sensitive detector 104 rotate about the center of rotation 114. The source 102 and detector 104 are generally mounted to a rotating gantry (not shown) for rotation about the examination region 106. In some embodiments, however, the source 102 and detector 104 may remain at a constant angular position while the object 108 is moved and/or rotated to produce the requisite angular sampling. While the figures and description are focused on the use of flat panel detectors, arcuate detectors or detectors having yet other shapes may also be used. Furthermore, while the figures and discussion focus on a CT system in which the source 102 is a point source, other alternatives are contemplated. For example, the source 102 may be a line source. Gamma and other radiation sources may also be used. Multiple sources 102 and detectors 104 may also be provided, in which case corresponding sets of sources and detectors may be offset angularly and/or longitudinally from one another.

In FIG. 1, the x-ray source 102 and detector 104 of the exemplary centered geometry 100 are depicted in two opposing positions in the transaxial plane, position A in solid lines and position B in dotted lines. In position B, the x-ray source 102 and detector 104 are rotated 180 degrees about the center of rotation 114 from position A. As both the x-ray source 102 and detector 104 of the exemplary centered geometry 100 are centered with respect to the center of rotation 114, the central ray 116 of the x-ray beam 112 and the detector center 119 are aligned with the center of rotation 114 when the x-ray source 102 and detector 104 are in both position A and position B.

Figure 2:
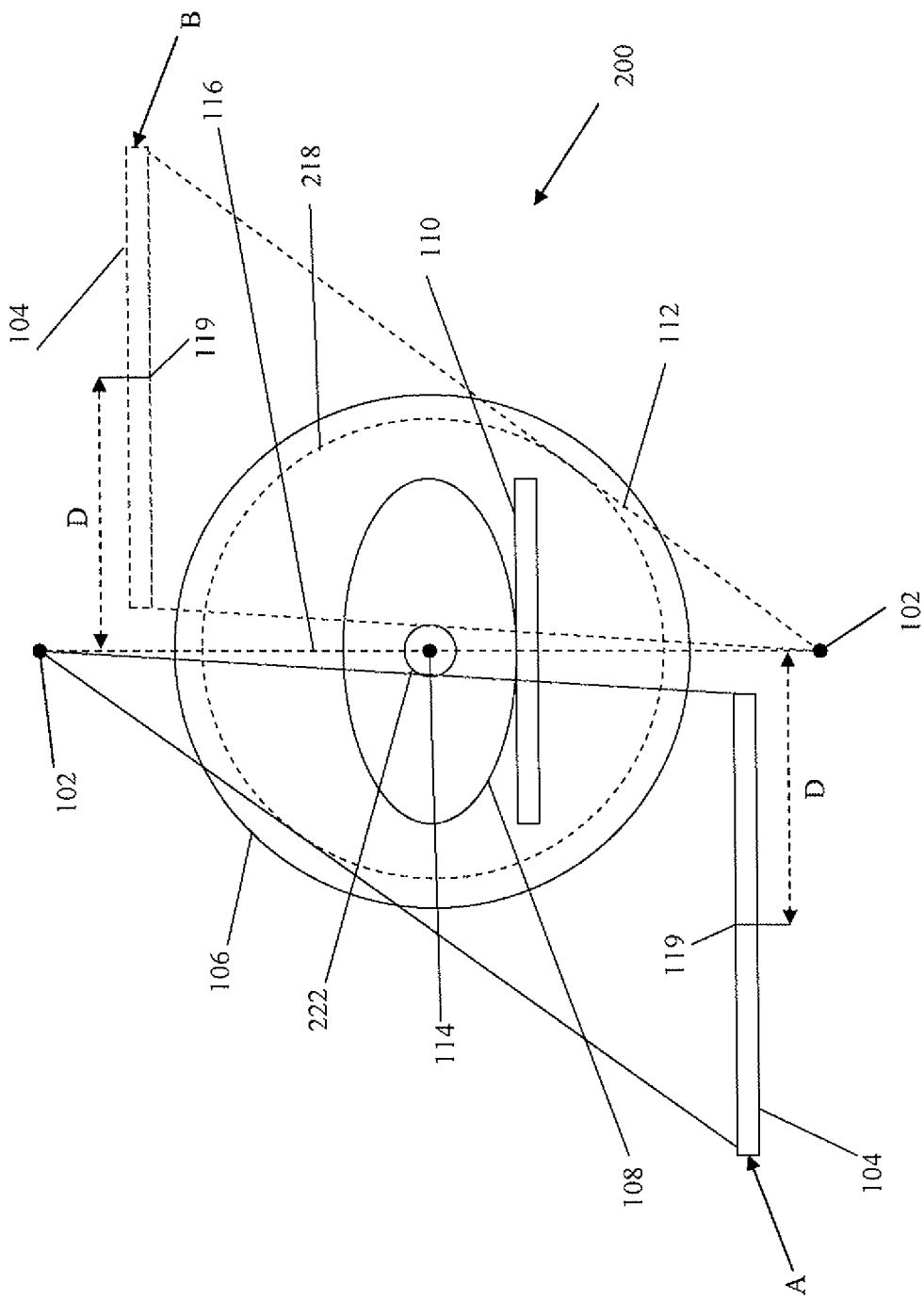
FIG. 2 is a transaxial view of an offset CT acquisition geometry according to an embodiment of the invention.

FIG. 2 depicts an exemplary offset geometry 200 for an imaging apparatus. The detector center 119 of the detector 104 of the exemplary offset geometry 200 is transversely displaced or offset from the center of rotation 114 in the transaxial plane by a distance D. As described previously in connection with the centered geometry 100, the x-ray source 102 and the x-ray sensitive detector 104 of the offset geometry 200 rotate about the center of rotation 114. In FIG. 2, the x-ray source 102 and detector 104 of the exemplary offset geometry 100 are depicted in two opposing positions in the transaxial plane, position A in solid lines and position B in dotted lines. In position B, the x-ray source 102 and detector 104 are rotated 180 degrees about the center of rotation 140 from position A. As illustrated in FIG. 2, the detector center 119 is offset from the center of rotation 114 in the transaxial plane by a distance D in both position A and position B.

The transverse FOV 218 of the offset geometry 200 is larger than the transverse FOV 118 of the centered geometry 100. The detector center 119 may be offset from the center of rotation 114 in the transaxial plane by various distances in different embodiments of the present invention by varying the distance D. For example, the detector center 114 may be offset from the center of rotation 119 by a distance D between 0 and 35 centimeters or greater. The distance D may approximate, or even exceed, the transverse half-width of the detector, so that there is a "hole" 222 in the center of the transverse FOV 218. The distance D may be varied in multiple ways to customize the size of the transverse FOV 218. The detector 104 may be shifted to vary the size of the transverse FOV 118 by any suitable means. For example, the detector 104 may be moved in various directions relative to the rotating gantry and the center of rotation 114 either manually by a human user or by a mechanical drive. It can be shifted linearly, as is useful with a flat panel detector, or rotationally, as is useful for a curved detector. While the exemplary offset geometry 200 described includes a centered source and an offset detector, it should be understood that additional CT imaging device geometries, which include an offset source or an offset source and an offset detector are contemplated.

Figure 2A:
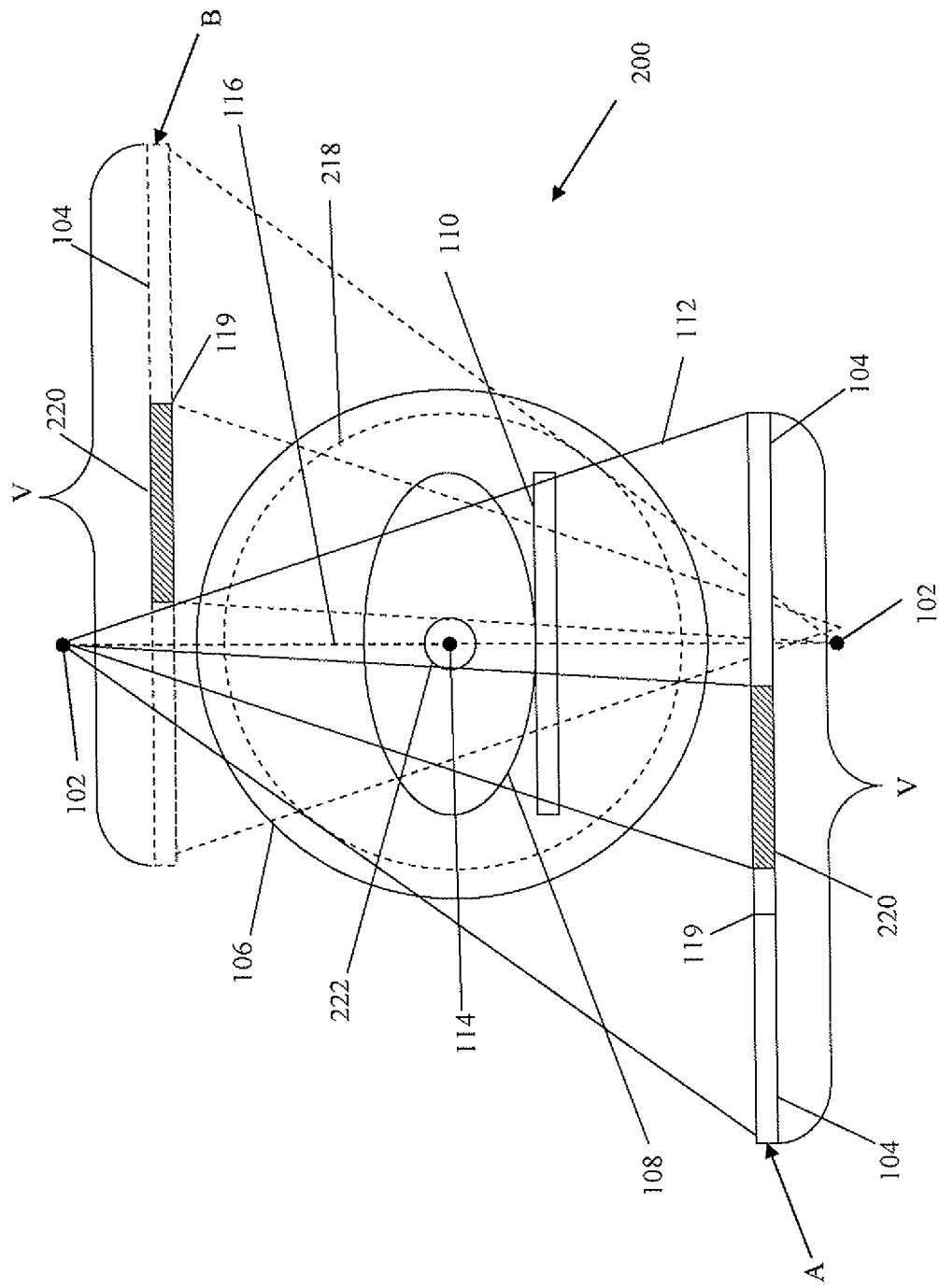
FIG. 2A is a transaxial view of a virtual detector which results from combining the data gathered from the centered geometry of FIG. 1 and the offset geometry of FIG. 2.

FIG. 2A depicts an overlay of the exemplary centered geometry 100 and the exemplary offset geometry 200. In FIG. 2A, the x-ray source 102 and detector 104 of the exemplary centered geometry 100 and exemplary offset geometry 200 are overlaid each other in two opposing positions in the transaxial plane, position A in solid lines and position B in dotted lines. The area of the detector 104 of the exemplary centered geometry 100 in position A that overlaps with the detector 104 of the exemplary offset geometry 200 in position A is indicated by the cross-hatched section 220 in FIG. 2A. Likewise, there is also an overlapping region 220 between the detector 104 of the exemplary centered geometry 100 in position B and the detector 104 of the exemplary offset geometry 200 in position B. During image reconstruction, the projection data obtained from the exemplary centered geometry 100 and exemplary offset geometry 200 can be combined together, as if they were measured by a single larger virtual detector V. This may be accomplished, for example, with faded weighting and/or averaging the projection data obtained in the overlapping region 220. In additional embodiments, projection data may not be obtained from a centered geometry and an offset geometry, but, rather, projection data may be obtained from two different offset geometries. For example, projection data could be obtained from a scan taken with the detector center 114 offset from the center of rotation 119 by a first distance D and a second set of projection data could be obtained from another scan taken with the detector center 114 offset from the center of rotation 199 by a second distance D.

Figure 3:
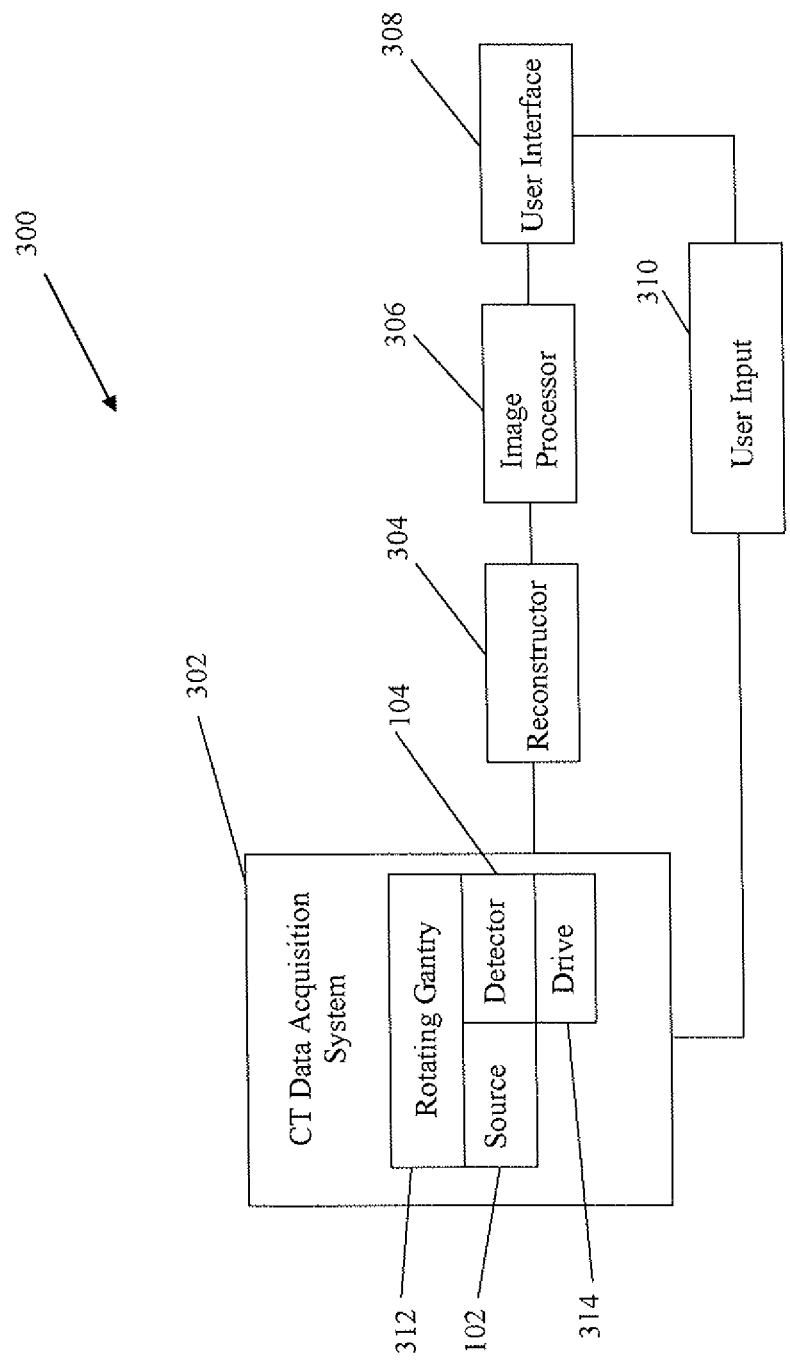
FIG. 3 is an imaging system according to an embodiment of the invention.

FIG. 3 depicts a CT imaging system 300 suitable for use with the exemplary centered geometry 100 and offset geometry 200 described above. The CT imaging system 300 includes a CT data acquisition system 302, a reconstructor 304, an image processor 306, a user interface 308, and a user input 310. The CT data acquisition system 302 includes the source 102 and detector 104, which are mounted to a rotating gantry 312 for rotation about the examination region. Circular or other angular sampling ranges as well as axial, helical, circle and line, saddle, or other desired scanning trajectories are contemplated. The embodiment of the CT imaging device system 300 illustrated in FIG. 3 includes a drive 318, such as a microstep motor, that provides the requisite force required to move the source 102 and/or detector 104.

The reconstructor 304 reconstructs the data generated by the data acquisition system 302 using reconstruction techniques to generate volumetric data indicative of the imaged subject. Reconstruction techniques include analytical techniques such as filtered backprojection, as well as iterative techniques. The image processor 306 processes the volumetric data as required, for example for display in a desired fashion on the user interface 308, which may include one or more output devices such as a monitor and printer and one or more input devices such as a keyboard and mouse.

The user interface 308, which is advantageously implemented using software instructions executed by a general purpose or other computer so as to provide a graphical user interface ("GUI"), allows the user to control or otherwise interact with the imaging system 300, for example by selecting a desired FOV configuration or dimension, initiating and/or terminating scans, selecting desired scan or reconstruction protocols, manipulating the volumetric data, and the like.

A user input 310 operatively connected to the user interface 308 controls the operation of the CT data acquisition system 302, for example to carry out a desired scanning protocol, optionally position the detector 104 and/or the source 102 so as to provide the desired FOV, and the like.

Figure 4:
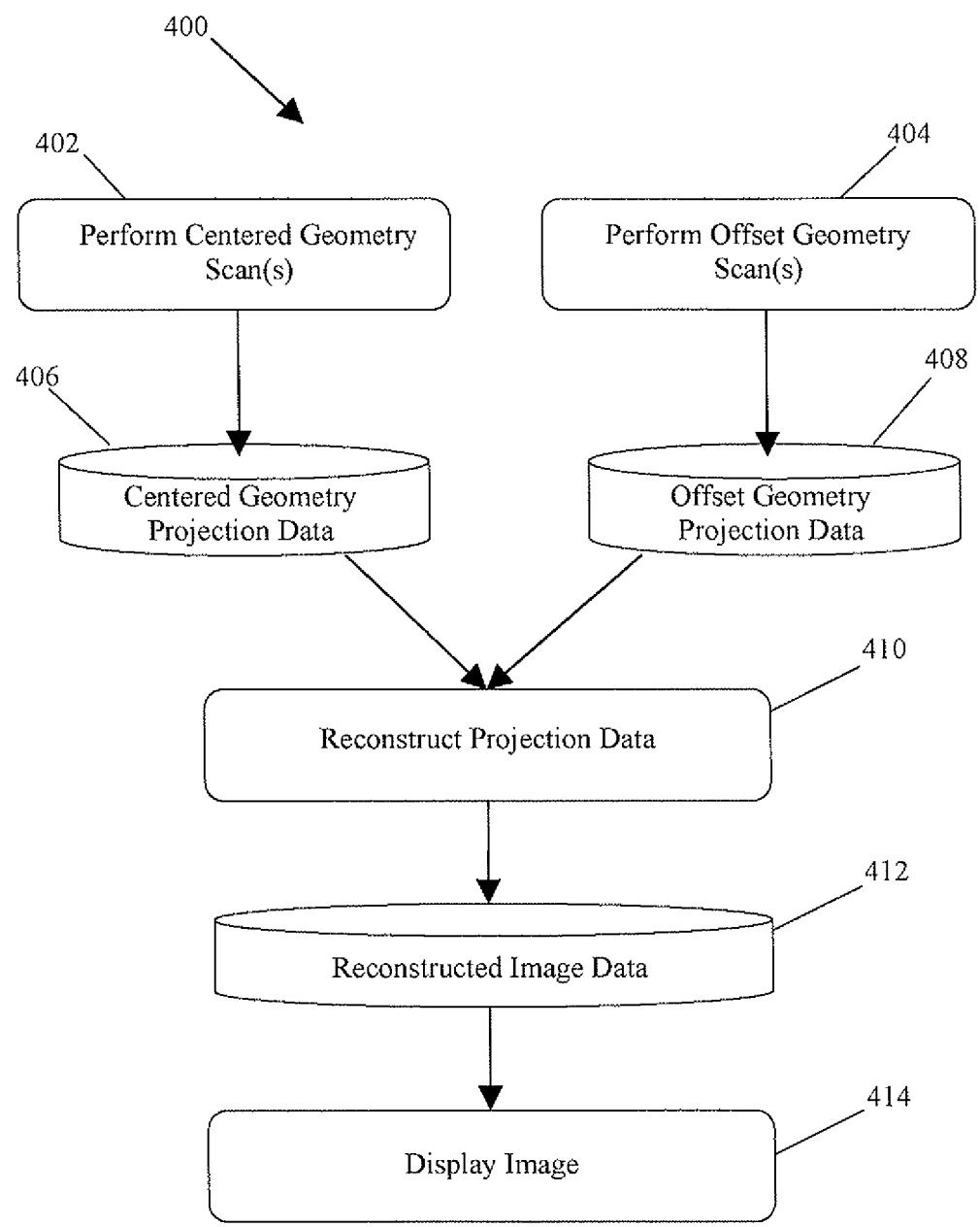
FIG. 4 depicts an imaging method according to an embodiment of the invention.

An exemplary imaging process 400 according to one aspect of the present invention is illustrated in FIG. 4. In step 402, the CT imaging system 300 is utilized to take at least one scan of the imaged subject with the source 102 and detector 104 in the centered geometry 100 to acquire projection data at a sufficient plurality of angular positions about the examination region 106. In step 404, at least one scan is taken by the CT imaging system 300 with the source 102 and detector 104 in an offset geometry 200. The order of steps 402 and 404 may be reversed, as the first scan(s) may be taken with the CT imaging system 300 in the offset geometry 200 followed by scan(s) with the CT imaging system 300 in the centered geometry 100. As discussed above, the detector 104 and/or the source 102 of the offset geometry 200 may be offset by a variety of distances D from the center of rotation 114 in the transaxial plane. In additional embodiments, one or more scanning procedures may be conducted with the detector 104 and/or the source 102 offset from the center of rotation 114 in the transaxial plane by a different distance D in each scan.

As shown in FIG. 4, centered geometry projection data 406 is obtained from the centered geometry scan(s) of step 402 and offset geometry projection data 408 is obtained from the offset geometry scan(s) of step 404. The reconstructor 304 reconstructs the centered geometry projection data 406 and offset geometry projection data 408 at step 410 using known reconstruction techniques currently used in connection with offset geometry CT imaging devices to generate volumetric data indicative of the imaged subject 108, i.e., reconstructed image data 412. During reconstruction, the centered geometry projection data 406 and the offset geometry projection data 408 are pair-wised stitched together using the overlapping region between the projection data 406 and 408 resulting from the overlapping region 220 of the detector 104 for the registration of the projection data 406 and 408 with each other. Faded weighting and/or averaging may be optionally applied in the overlap regions of the centered geometry projection data 406 and the offset geometry projection data 408 during the reconstruction process. The combined reconstruction of the projection data 406 and 408 emulates a single scan with the large virtual detector V illustrated in FIG. 2A.

The reconstructed image data 412 obtained from step 410 is processed by the image processor 306. The resulting reconstructed image is displayed on the user interface 308 at step 414.

Existing CT imaging devices with offset geometries often suffer from image quality problems due to a limited data redundancy between opposite viewing directions, especially if the detector offset is large. Insufficient redundancies can visibly degrade image quality during reconstruction. These image degrading effects encountered with existing CT imaging devices utilizing offset geometries are largely avoided with the apparatus and method disclosed herein, because an even larger field of view can be achieved while significant redundancy between opposite virtual enlarged views is nevertheless guaranteed. Specifically, an "overlap" between opposite virtual enlarged views of half the actual detector width can easily be achieved, minimizing the likelihood and effect of artifacts occurring as a result of approximations made in the reconstruction for an off-center geometry.

The fact that the image acquisition method disclosed herein involves the usage of at least two scanning operations provides certain freedom with the distribution of radiation dosage during the scanning procedures. Different levels of radiation dosage may be associated with each of the scan(s) of step 404 and 402 as desired by the operator of the CT imaging device 300. For example, the offset geometry scan(s) of step 404 may be adapted to deliver less than half of the radiation dosage that is used in connection with the centered geometry scan(s) of step 402. Such dosage techniques can result in a better contrast-to-noise ratio being obtained for the centered geometry scan(s) of step 402. At the same time, the border areas of the imaged subject scanned by the offset geometry scan(s) of step 404, which are less relevant for medical diagnosis but useful for attenuation correction, will be exposed to relatively less radiation. In this manner, the radiation dosage delivered to a patient during the scanning procedures of steps 402 and 404 can be tailored to be generally equivalent or less than the radiation dosage delivered to a patient during a single scan with a wide detector, such as those used in helical CT imaging.

Another aspect of the present invention is directed generally to a method and apparatus for the detection, estimation and/or compensation of motion artifacts encountered when reconstructing tomographic images. In accordance with this aspect, a method and apparatus are provided for generating a motion map. The motion map is utilized to indicate which image regions may be corrupted by motion artifacts and/or for motion estimation and motion compensation to prevent or diminish motion artifacts in the reconstructed tomographic image.

Figure 5:
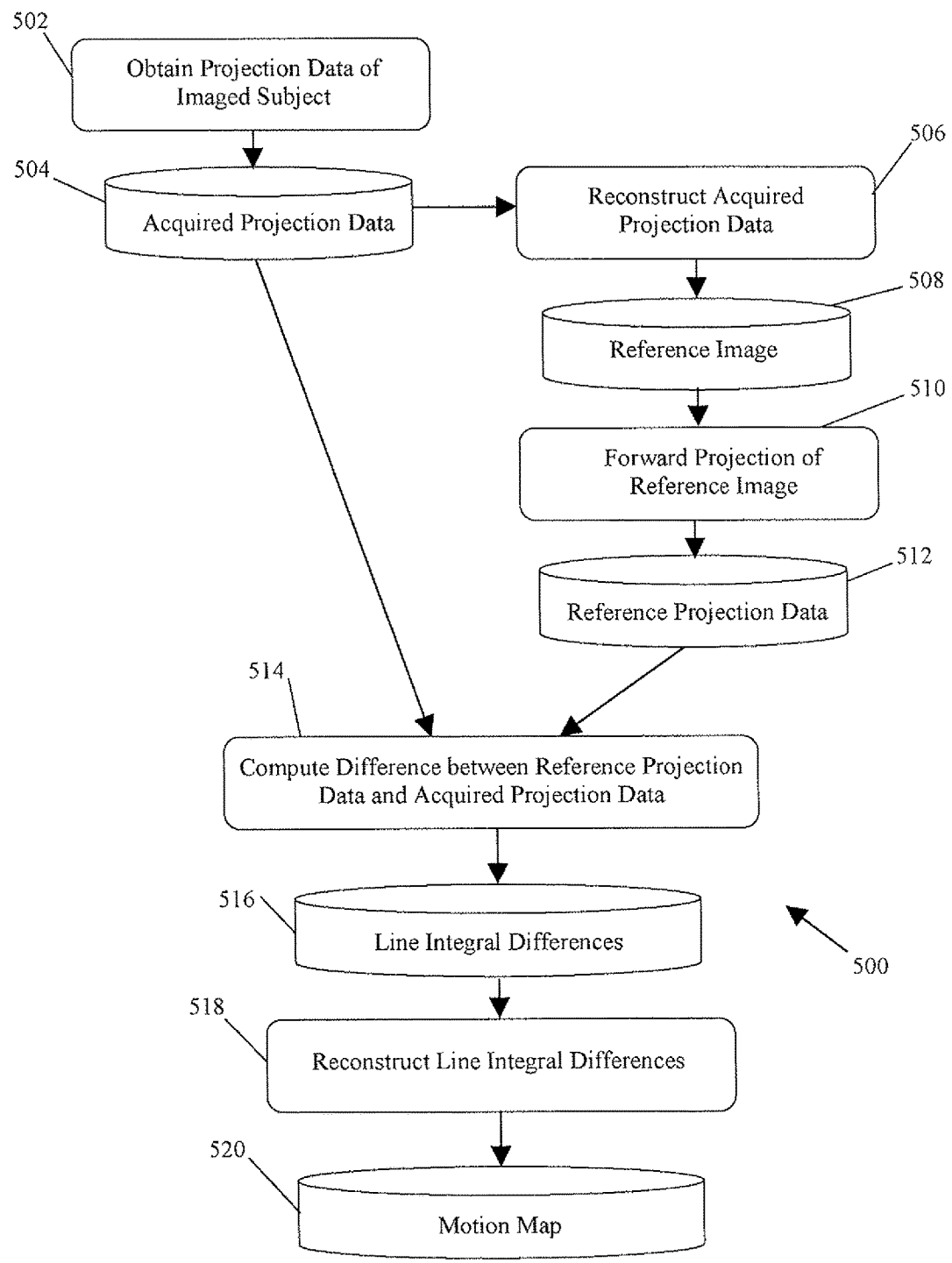
FIG. 5 depicts a method for detecting motion according to an embodiment of the invention.

An exemplary method 500 of detecting motion in reconstructed tomographic images according to one aspect of the present invention is illustrated in FIG. 5. At step 502, the CT imaging system 300 is used to obtain a set of acquired projection data 504 of the imaged subject 108. At step 506, tomographic reconstruction is applied to this acquired projection data 504 using known reconstruction techniques, such as filtered backprojection (FBP), to generate a reconstructed image (i.e., the "reference" image) 508. The reference image 508 may have artifacts as a result of object movement during the scanning process. At step 510, known forward projection techniques are applied to the previously reconstructed reference image 508 to derive reference projection data 512. Although the computation of reference projection data by the forward projection of a reconstructed image is a conventional aspect of iterative image reconstruction, it should be understood by those skilled in the art that the accuracy of image space interpolations and the possible truncation of projections are two important potential issues that may need to be addressed during this process. Furthermore, if the reference image 508 is reconstructed using the classical Feldkamp-Davis-Kress (FDK) algorithm, cone beam artifacts may corrupt the reference projections and hence should be accounted for.

Next, at step 514, the line integral differences 516 between the acquired projection data 504 and the reference projection data 512 are computed. Any such differences likely result from artifacts caused by movement of the object during the imaging scan 502. The line integral differences 516 between the acquired projection data 504 and the reference projection data 512 are computed independently for each pair of corresponding projections from the acquired projection data 504 and reference projection data 512. A data correction step could be optionally employed at this stage using, for example, the Helgason-Ludwig conditions or other similar data correction measures to correct any data inconsistencies. The line integral differences 516 represent an isolation of motion that occurred during the scanning procedure 502 in projection space.

Figure 7:
FIG. 7 is exemplary image generated by a software program depicting a motion map in accordance with an embodiment of the present invention.

At step 518, tomographic reconstruction is applied to the absolute values of the line integral differences 516 using known reconstruction techniques, such as filtered backprojection (FBP). The resulting image that is generated is a motion map 520, which is representative of the regions of the image 508 which are corrupted by motion that occurred during the scanning procedure 502. Thus the motion map 520 represents an isolation of the motion that occurred during the scanning procedure 502 in image space. The motion map 520 could be adapted to be a binary motion map that simply indicates whether or not motion exists in a given image voxel. Alternatively, a refined motion map 520 could indicate the amplitude of the motion that exists in any given image voxel. An exemplary motion map 520 is illustrated in FIG. 7. It should be understood by those skilled in the art that the exemplary method 500 of generating a motion map 520 may be an iterative process in additional embodiments.

Figure 6A:
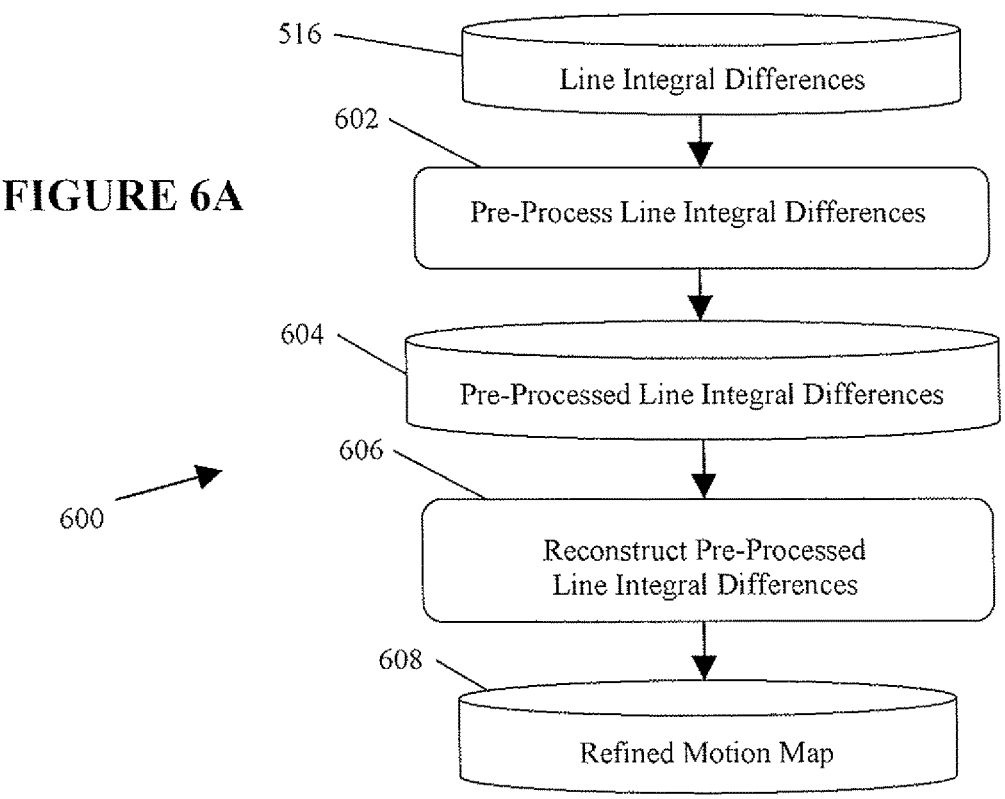
FIGS. 6A and 6B depict optional methods for refining a motion map in accordance with an embodiment of the present invention.

An optional exemplary method 600 for refining the motion map 520 in accordance with an embodiment of the present invention is illustrated in FIG. 6A. At step 602, the line integral differences 516 may be processed or refined, such as for example by windowing, normalization, or filtering, to produce pre-processed line integral differences 604. A windowing refinement is a non-linear mapping of input values to modified output values, where input values below a given minimum value and above a given maximum value are ignored or set to zero. As a special form of windowing, thresholding may be applied, where input values below a given threshold are set to zero and values above the threshold are set to one. Another sort of refinement is normalization, wherein the line integral differences are transformed to values between 0 and 1 to standardize and simplify subsequent mathematical calculations. Yet another sort of refinement is to apply a volumetric median filter, a Gaussian blur, or some other filtering process. In one exemplary embodiment, the size of the neighborhood for the volumetric median filter and the size of the convolution kernel for the Gaussian blur are set to 3×3×3. The pre-processing refinement 602 may also involve other kinds of image processing in additional embodiments.

The pre-processed line integral differences 604 are reconstructed using known reconstruction techniques, such as filtered backprojection (FBP), at step 606. The resulting image that is generated is a refined motion map 608, that has been windowed, normalized, filtered, or otherwise refined. The refined motion map 608 could be adapted to be either a binary motion map that simply indicates whether or not motion exists in a given image voxel or the refined motion map 608 could indicate the amplitude of the motion that exists in any given image voxel.

Figure 6B:
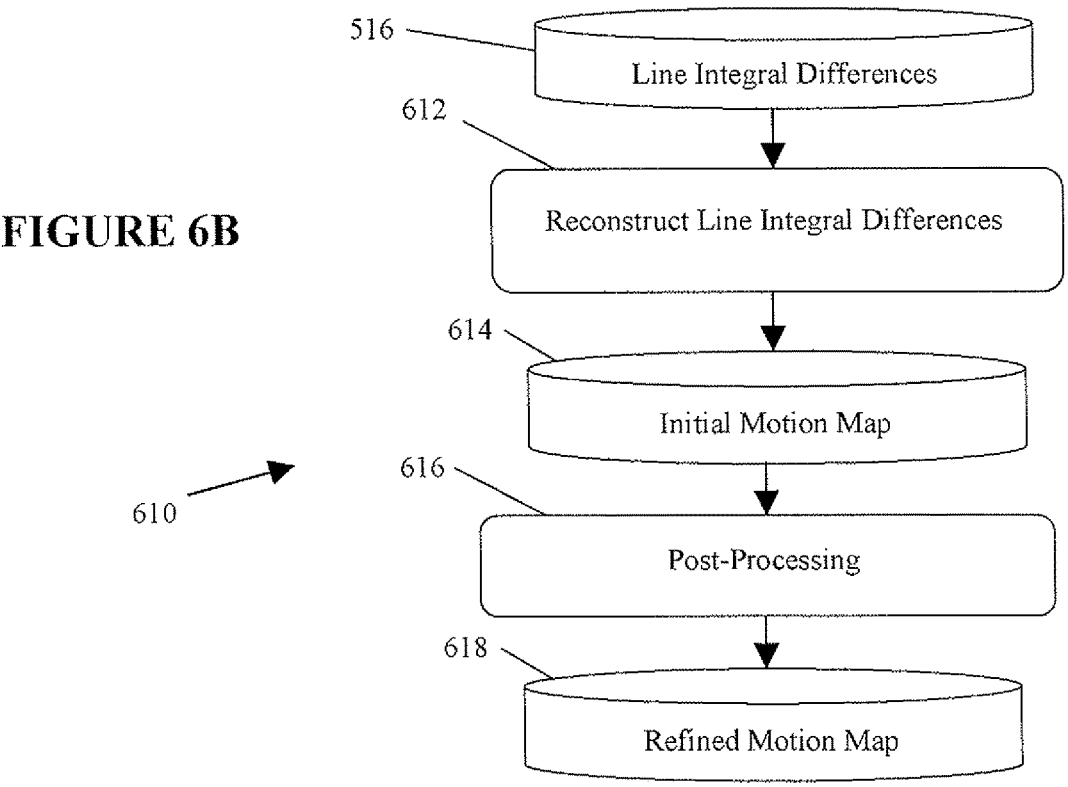

Another optional exemplary method 610 for refining the motion map 520 in accordance with an embodiment of the present invention is illustrated in FIG. 6B. At step 612, the line integral differences 516 are reconstructed using known reconstruction techniques, such as filtered backprojection (FBP). The resulting image that is generated is an initial motion map 614. The initial motion map 614 is then processed or refined at step 616, such as for example by windowing, normalization, filtering, to produce a post-processed refined motion map 618. For example, in one exemplary embodiment the initial motion map 614 is thresholded at 150 Hounsfield units (HU). Such processing or refining of the motion map 614 serves to remove "reconstruction noise" or other inconsistencies in the data and to avoid streaking.

A motion map such as the motion map 520, 608 or 618 has multiple uses. For example, the motion map can be used as a reference by a radiologist or other individual performing the imaging process to indicate which voxels of a particular reconstructed image could potentially contain reconstruction artifacts due to motion, e.g., regions of an image with potential motion artifacts that cause them to be unsuitable for diagnosis or localization. In this manner, the motion map serves as a reliability indicator to be used in conjunction with a reconstructed image, as it supplies information about the location of in-scan motion present in the reconstructed image.

In addition, the motion map can be combined with a motion estimation and compensation scheme to apply local motion correction during image reconstruction. Conventional global motion compensation techniques are applied universally to the entire image during the reconstruction process. This can result in artifacts being introduced into regions of the reconstructed image which were not affected by any motion. As a result, in practice, these global motion compensation methods can corrupt static regions of reconstructed images with artifacts resulting from incorrect motion compensation.

Figure 8:
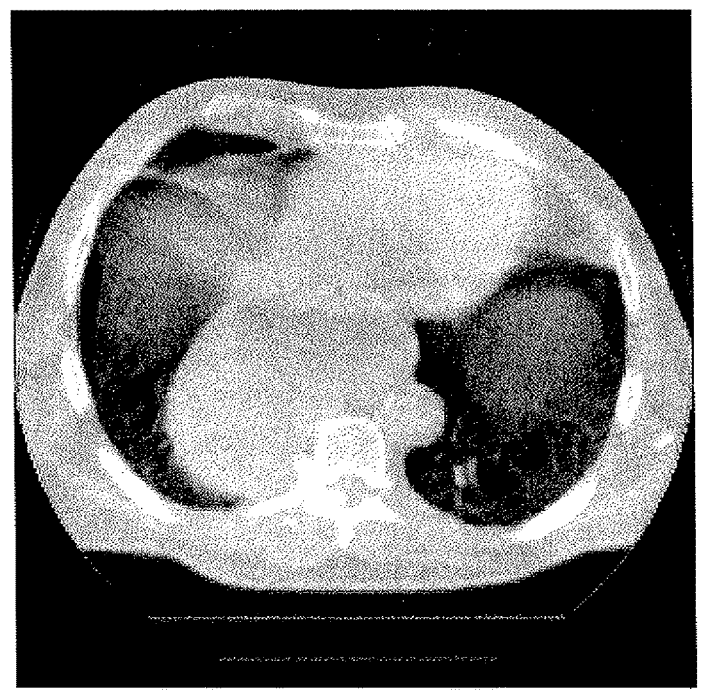
FIG. 8 is an exemplary image generated by a software program depicting a motion-corrupted reconstructed image without any motion correction.
Figure 9:
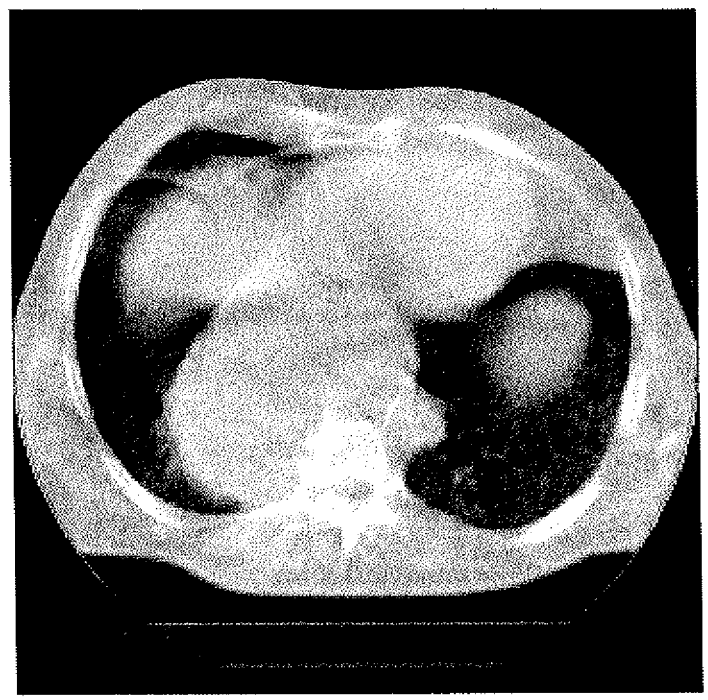
FIG. 9 is an exemplary image generated by a software program depicting the reconstructed image of FIG. 8 after a global motion correction.
Figure 10:
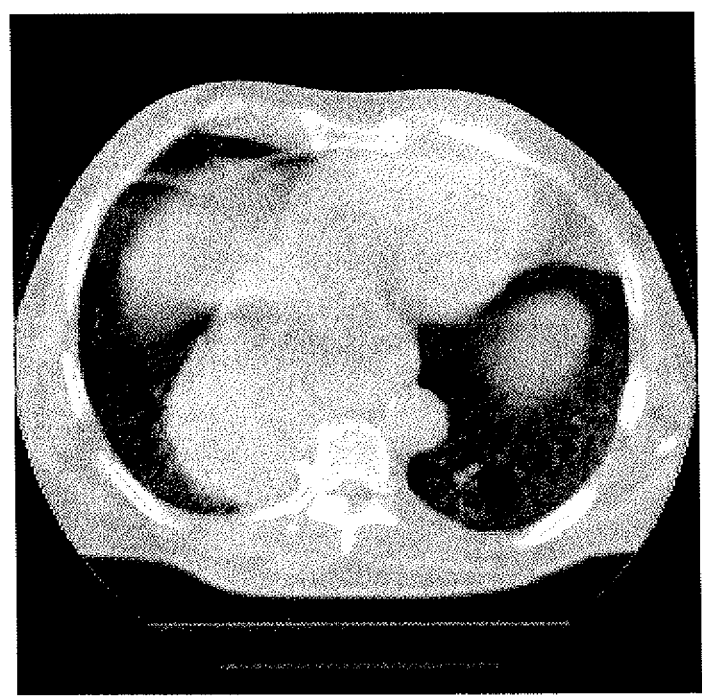
FIG. 10 is an exemplary image generated by a software program depicting the reconstructed image of FIG. 8 after a local motion correction.

However, the use of the motion map in conjunction with local motion correction prevents the application of motion compensation in static regions where no motion occurred during the scanning procedure. This can prevent artifacts in such static regions. For example, the motion map could be used as a "blending map" with motion correction techniques being applied only in those areas which are indicated to have experienced motion based upon the motion map. Furthermore, the motion map could also be used as a "weighting map." Under this approach, the motion map would be used to determine a "weighted" amount of motion correction that would be applied to any given image voxel, which would be an adjusted value between zero motion correction being applied and, at most, the amount of motion correction that would be applied under current conventional global motion correction techniques. Still further uses and applications of the motion map will be appreciated by those of ordinary skill in the art. To further illustrate the application of the motion compensation techniques described herein, an exemplary motion-corrupted image generated by a software program is illustrated in FIG. 8. FIG. 9 is a reconstruction of the image in FIG. 8 that has undergone global motion correction. FIG. 10 is a reconstruction of the image in FIG. 8 that has undergone local motion correction using a motion map.

The aforementioned functions, such as for example, selecting a desired FOV configuration or dimension, initiating and/or terminating scans, selecting desired scan or reconstruction protocols, manipulating the volumetric data, and the like, can be performed as software logic. "Logic," as used herein, includes but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), or other programmed logic device. Logic may also be fully embodied as software.

"Software," as used herein, includes but is not limited to one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, and/or the desires of a designer/programmer or the like.

The systems and methods described herein can be implemented on a variety of platforms including, for example, networked control systems and stand-alone control systems. Additionally, the logic, databases or tables shown and described herein preferably reside in or on a computer readable medium, such as a component of the imaging system 300. Examples of different computer readable media include Flash Memory, Read-Only Memory (ROM), Random-Access Memory (RAM), programmable read-only memory (PROM), electrically programmable read-only memory (EPROM), electrically erasable programmable read-only memory (EEPROM), magnetic disk or tape, optically readable mediums including CD-ROM and DVD-ROM, and others. Still further, the processes and logic described herein can be merged into one large process flow or divided into many sub-process flows. The order in which the process flows herein have been described is not critical and can be rearranged while still accomplishing the same results. Indeed, the process flows described herein may be rearranged, consolidated, and/or re-organized in their implementation as warranted or desired.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An apparatus for generating a motion map, the apparatus comprising:
   a radiation source;
   a radiation sensitive detector which detects radiation emitted by the source that has traversed an examination region; and
   a reconstructor and an image processor;
   wherein the radiation source and the radiation sensitive detector are used to acquire projection data at a plurality of angular positions relative to an object disposed in the examination region;
   wherein the reconstructor is used to generate a reference image from the projection data;
   wherein reference projection data is obtained from a forward projection of the reference image;
   wherein differences between the acquired projection data and the reference projection data are computed to determine line integral differences; and
   wherein the image processor uses the line integral differences to generate a motion map indicative of the regions of a corresponding image reconstructed from the projection data that are affected by motion.

2. The apparatus of claim 1, wherein the image processor applies a windowing process to refine the motion map.

3. The apparatus of claim 1, wherein the image processor applies a normalization process to refine the motion map.

4. The apparatus of claim 1, wherein the image processor applies a volumetric median filter to refine the motion map.

5. The apparatus of claim 1, wherein the image processor applies a Gaussian blur to refine the motion map.

6. The apparatus of claim 1, wherein the apparatus is a cone-beam computed tomography imaging device.

7. The apparatus of claim 1, wherein the image processor processes the volumetric data for display on a user interface.

8. The apparatus of claim 1, wherein the motion map indicates the amount of motion correction to be applied to an image.

9. The apparatus of claim 8, wherein the image processor uses the motion map in a motion-compensated image reconstruction.

10. The apparatus of claim 9, wherein the image processor performs a reconstruction as a weighted average between a motion corrected reconstruction and a reconstruction not corrected for motion, wherein the weights are provided by the motion map.

11. The apparatus of claim 8, wherein the motion displacement in a motion-corrected reconstruction is adapted according to the motion map.

12. A method for generating a motion map, the method comprising the steps of:
   acquiring, by a radiation sensitive detector, projection data at a plurality of angular positions relative to an object disposed in an examination region;
   reconstructing, by a reconstructor, from the projection data to generate a reference image;
   obtaining reference projection data from a forward projection of the reference image;
   computing differences, by an image processor, between the acquired projection data and the reference projection data to determine line integral differences; and
   using the line integral differences to generate a motion map indicative of the regions of a corresponding image reconstructed from the projection data that are affected by motion.

13. The method of claim 12, further comprising the step of applying a windowing process to refine the motion map.

14. The method of claim 12, further comprising the steps of refining the motion map by normalizing the motion map, applying a volumetric median filter to the motion map, and applying a Gaussian blur to the motion map.

15. The method of claim 12, further comprising the step of using the motion map in conjunction with the corresponding image reconstructed from the projection data to detect regions of the reconstructed image that are affected by motion.

16. The method of claim 12, further comprising the step of using the motion map in conjunction with a motion correction technique to compensate for the effects of motion in the corresponding image reconstructed from the projection data.

17. The method of claim 16, further comprising compensating for motion only in regions of the corresponding image that are indicated to have been affected by motion by the motion map.

18. The method of claim 16, further comprising compensating for motion by applying a weighted value of motion correction to regions of the corresponding image reconstructed from the tomographic projection data, the weighted value being calculated for each region based upon a quantitative amount of motion indicated for each image region by the motion map.

19. A method for generating a motion map, the method comprising the steps of:

acquiring, by a radiation sensitive detector, projection data at a plurality of angular positions relative to an object disposed in an examination region;

reconstructing, by a reconstructor, from the projection data to generate a reference image;

obtaining reference projection data from a forward projection of the reference image;

computing differences, by an image processor, between the acquired projection data and the reference projection data to determine line integral differences; and using the line integral differences to generate a motion map indicative of the regions of a corresponding image reconstructed from the projection data that are affected by motion;

wherein acquiring projection data comprises acquiring projection data during at least two scanning procedures including centered geometry projection data during a centered geometry scanning procedure and offset geometry projection data during an offset geometry scanning procedure, wherein the centered geometry projection data and the offset geometry projection data include an overlap region from opposite views of the object, and wherein reconstructing comprises reconstructing the projection data acquired during the at least two scanning procedures together to generate volumetric data indicative of the object, wherein the centered geometry projection data and the offset geometry projection data are registered based on the overlap region.

* * * * *